United States Patent [19]

Schneider et al.

[11] Patent Number: 5,202,443

[45] Date of Patent: Apr. 13, 1993

[54] PROCESS FOR PREPARING 1-(2S)-3MERCAPTO-METHYL-1-OXO-PROPYL)-L-PROLINE

[75] Inventors: Géza Schneider; Gábor Blaskó; Agnes Kovács née Palotai; Gabriella Ürmös née Lassu; Judit Kun; Ilma Dinnyés née Nagy; Ivan Beck; Elemér Jákflavi; András Dietz, all of Budapest, Hungary

[73] Assignee: EGIS Gyôgyszergyâr, Budapest, Hungary

[21] Appl. No.: 762,688

[22] Filed: Sep. 20, 1991

[30] Foreign Application Priority Data

Sep. 21, 1990 [HU] Hungary ............... 5998/90

[51] Int. Cl.$^5$ .......................... C07D 207/09
[52] U.S. Cl. ........................ 548/533
[58] Field of Search .................... 548/533

[56] References Cited

U.S. PATENT DOCUMENTS

| | | | |
|---|---|---|---|
| 4,105,776 | 8/1978 | Ondetti et al. | 548/533 X |
| 4,192,945 | 3/1980 | Ondetti | 548/533 X |
| 4,241,076 | 12/1980 | Ondetti et al. | 548/533 X |
| 4,332,725 | 6/1982 | Fischer et al. | 548/533 |
| 4,684,660 | 8/1987 | Ondetti et al. | 548/533 X |
| 5,002,964 | 3/1991 | Loscalzo | 548/533 X |
| 5,025,001 | 6/1991 | Loscalzo et al. | 548/533 X |

FOREIGN PATENT DOCUMENTS 387381 1/1989 Austria.

OTHER PUBLICATIONS

Cushman, et al.; Biochemistry, 16, (1977), pp. 5184-5491.

*Primary Examiner*—Joseph Paul Brust
*Attorney, Agent, or Firm*—Beveridge, DeGrandi & Weilacher

[57] ABSTRACT

The invention relates to a novel process for preparing 1-[(2S)-3-mercapto-2-methyl-1-oxopropyl]-L-proline (captopril) of formula (I).

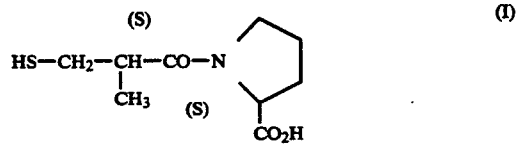

which comprises hydrogenolysing 1-[(2S)-2-methyl-1-oxo-3-rhodanidopropyl]-L-proline of formula (II)

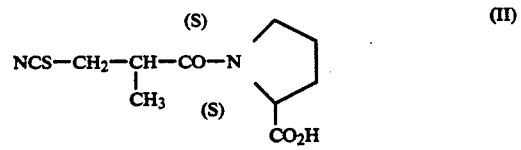

in an inert solvent, in the presence of a catalyst, at a temperature of 50° to 120° C. under a pressure of $10^5$ to $10^7$ Pa.

The above compound of formula (II) is new and can be prepared by acylating L-proline with a reactive acylating derivative of (2S)-2-methyl-3-rhodanido-propionic acid of formula (III).

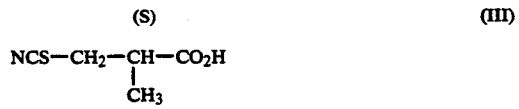

5 Claims, No Drawings

PROCESS FOR PREPARING 1-(2S)-3MERCAPTO-METHYL-1-OXOPROPYL)-L-PROLINE

This invention relates to a new process for preparing 1-[(2S)-3-mercapto-2-methyl-1-oxopropyl]-L-proline of the formula (I)

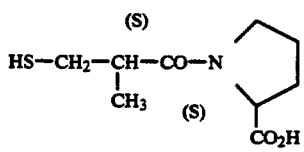

(generic name: captopril), a known antihypertensive drug.

A high number of processes are known for the preparation of the compound of formula (I). A common feature of the major part of them consists in that a (2-methyl-1-oxopropyl)-L-proline derivative containing the mercapto group in a protected or masked form is prepared to obtain the product after removing the protective group or forming the free mercapto group from its masked form. In these processes the separation of the desired (2S,2S) isomer has also to be solved.

Thus, according to the United States patent specification No. 4,105,776 or a publication [Biochemistry 16, 5484 (1977)] dealing with one of the process variants described therein in more detail, L-proline is transformed to tertiary-butyl L-prolinate, which is acylated with 3-acetylthio-2-methyl-propionic acid in the presence of N,N'-dicyclohexyl-carbodiimide, then the acylated product is resolved through its dicyclohexyl-amine salt, 1-[(2S)-3-acetyl-thio-2-methyl-1-oxopropyl]-L-proline is separated and finally the protective group is removed by hydrolysis. The overall yield calculated for L-proline is only about 10%.

According to the United States patent specification No. 4,332,725 L-proline is acylated with a 3-halo-2-methylpropionyl chloride, the desired 1-[(2S)-3-halo-2-methyl-1-oxopropyl]-L-proline isomer is directly separated and transformed to Bunte's salt by using an alkali metal thiosulfate to obtain captopril by the acidic hydrolysis of the latter salt. In this way an overall yield of about 30 % calculated for L-proline is achieved.

The Austrian patent specification No. 387,381 describes the reaction of 1-[(2S)-3-halo-2-methyl-1-oxopropyl]-L-proline with thiourea to give the corresponding isothiuronium derivative which is then hydrolized to captopril, resulting in an overall yield of 34 to 35 % calculated for L-proline.

The aim of the present invention was to provide a process for the preparation of captopril, which renders possible to produce this compound in a simple way, with a yield over 50 % calculated for L-proline.

Now it has been found that this aim can be achieved by hydrogenating 1-[(2S)-2-methyl-1-oxo-3-rhodanidopropyl]-L-proline of the formula (II)

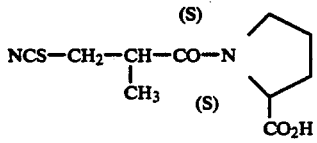

in an inert solvent in the presence of a catalyst, at a temperature of 50° to 120 ° C. under a pressure of $10^5$ to $10^7$ Pa.

In this description "inert solvent" means a solvent or solvent mixture which, on the one hand, dissolves both captopril formed by hydrogenation and preferably also the starting compound of formula (II), without reacting with any of them and, on the other hand, is not reduced during the catalytic hydrogenation.

Organic solvents, e.g. esters such as ethyl acetate or butyl acetate, halogenated hydrocarbons such as methylene dichloride, dichloroethane or chloroform and the like are preferably used as inert solvents. The mixture of several organic solvents may also serve as inert solvent. The organic solvent may contain water, too, either in dissolved state, i.e. in homogeneous phase, or in heterogeneous phase when the organic solvent is water-immiscible.

Palladium on charcoal is preferably used as hydrogenating catalyst usually in an amount of 1 to 20 % calculated for the weight of the starting substance of formula (II).

It is suitable to carry out the catalytic hyhdogenation in a temperature range of 50° to 120 ° C., preferably at 70° to 90 ° C., under a pressure of $10^5$ to $10^7$ Pa, advantageously $(5-6) \times 10^5$ Pa.

The obtained captopril of formula (I) is separated by using common methods of the preparative organic chemistry. Preferably, after completing the catalytic hydrogenation the catalyst is removed by filtration, the solution containing the aimed product is evaporated or concentrated and captopril is crystallized. When being present, water may be separated from the water-immiscible organic solution. A small amount of water can be bound by using an anhydrous drying agent, e.g. magnesium sulfate.

The catalyst employed is suitably re-actived and repeatedly used in a next hydrogenation step.

1-[(2S)-2-methyl-1-oxo-3-rhodanidopropyl]-L-proline of formula (II) used as starting substance in the process of the invention is a novel compound which is prepared by the acylation of L-proline with a reactive acylating derivative of (2S)-2-methyl-3-rhodanidopropionic acid of formula (III).

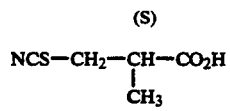

Suitable reactive acylating derivatives are the mixed anhydrides of the general formula (V),

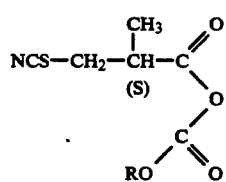

wherein R stands for a $C_{1-5}$alkyl or benzyl group.

The mixed anhydride of the general formula (V) is prepared by reacting (2S)-2-methyl-3-rhodanidopropionic acid of the formula (III) with a chloroformate ester of the general formula (IV),

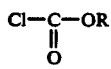

wherein R is as defined above, in the presence of an acid-binding agent.

(2S)-2-Methyl-3-rhodanidopropionic acid of formula (III) is prepared by reacting an isobutyric acid derivative of the general formula (VI)

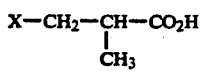

wherein X stands for an $R^1$—$SO_2$—O— group containing a $C_{1-4}$alkyl or an optionally methyl-substituted phenyl moiety as $R^1$, with a rhodanide of the general formula (VII),

wherein A means an alkali metal or an alkali earth metal atom or a group of the general formula (a),

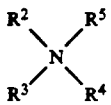

wherein $R^2$, $R^3$, $R^4$ and $R^5$, independently from each other, represent hydrogen, $C_{1-4}$alkyl or benzyl group, and then resolving the 2-methyl-3-rhodanidopropionic acid obtained.

The resolution of 2-methyl-3-rhodanidopropionic acid is preferably achieved by using (αS)-methyl-benzomethanamine.

By using the process according to the invention a yield of about 95 % can be realized. Therefore, the overall yield calculated for L-proline is about 57 %. Thus, the process of the invention is essentially more economical than the processes known in the art; it consists of only a low number of steps to give captopril of very high purity.

The process of the invention is illustrated in detail by the following non-limiting Exmples.

EXAMPLE 1

Preparation of 1-[(2S)-3-mercapto-2-methyl-1-oxopropyl]-L-proline

After adding 2.42 g of 10% palladium-on-charcoal catalyst to a solution containing 24.23 g of 1-[(2S)-2-methyl-1-oxo-3-rhodanidopropyl]-L-proline in 240 ml of ethyl acetate the mixture is hydrogenated at 80° C. under a pressure of $5 \times 10^5$ Pa for 8 hours while stirring. Subsequently the catalyst is removed by filtration and washed with ethyl acetate. The ethyl acetate solution obtained is evaporated to 70 ml under reduced pressure and the residue is cooled to 0° C. The crystalline precipitate is filtered and washed under nitrogen with cooled ethyl acetate to obtain 19.99 g (92%) of the aimed product, m.p.: 106°-108° C., $[\alpha]_D^{25}$ −133° (c=0.5, ethanol).

EXAMPLE 2

Preparation of 1-[(2S)-3-mercapto-2-methyl-1-oxopropyl]-L-proline

The process described in Example 1 is followed, except that 1-[(2S)-2-methyl-1-oxo-3-rhodanidopropyl]-L-proline is hydrogenated in a mixture containing 120 ml of methylene chloride and 120 ml of water. After filtering the catalyst the aqueous phase is separated and the organic phase is worked up as described in Example 1 to give the aimed product in a yield of 20.64 g (95 %), m.p.: 106°-108° C., $[\alpha]_D^{25}$ −133° (c=0.5, ethanol).

The starting compound is prepared as follows.

Preparation of 2-methyl-3-rhodanidopropionic acid

A solution of 16.7 g of 3-bromo-2-methylpropionic acid in 50 ml of toluene is cooled to 0° C. and 19.42 g of potassium rhodanide as well as 5 ml of water are added. The pH value of the reaction mixture is adjusted to 6.5 by dropwise adding 10 N sodium hydroxide solution. The pale yellow biphasic solution obtained is stirred at 25° C. for 48 hours while maintaining the pH value between 6.4 and 6.6 by dropwise adding a further amount of sodium hydroxide solution. After cooling down the reaction mixture to 0° C and adjusting the pH value to 2.7 by 10 N sulfuric acid the mixture is filtered and the organic phase is separated. The aqueous phase is extracted five times with 20 ml of toluene each and after combining the organic phase is washed with 10 ml of water. The pale yellow toluene solution is dried over anhydrous magnesium sulfate and evaporated under reduced pressure to obtain the aimed product in a yield of 11.13 g (76.7 %), m.p. 24°-25° C. Based on determination by gas chromatography, the purity of this product is 98 to 99 %. IR spectrum (film): $\nu_{NCS}$ =2157 $cm^{-1}$.

Preparation of (2S)-2-methyl-3-rhodanidopropionic acid

A) Preparation of (2S)-2-methyl-3-rhodanidopropionic acid (αS)-methyl-benzomethanamine salt 8.48 g of (αS)-methyl-benzomethanamine dissolved in 16.5 ml of toluene are dropwise added to a solution containing 14.52 g of racemic 2-methyl-3-rhodanidopropionic acid in 20 ml of toluene during 5 minutes while stirring. During the addition the temperature increases from 26° C. to 46° C. The pale yellow solution obtained is maintained at 50° C. for one hour, then cooled to 25° C. and 1.33 g of the aimed product are added. After stirring the crystalline suspension obtained at 0° C. for one hour the mixture is filtered, the crystals are washed three times with 10 ml of cooled toluene each and dried to give the aimed salt in a yield of 10.91 g (72%), m.p.: 90.2°-91.8° C., $[\alpha]_D^{25}$ −54.8° (c=1, water). The optical purity of this salt is 93 %.

After repetition of the resolution process a product of 99% optical purity is obtained, m.p.: 92°-94° C.

B) Preparation of (2S)-2-methyl-3-rhodanidopropionic acid.

26.63 g of a twice resolved product obtained as described under A) above are dissolved in 100 ml of water, then 100 ml of ethyl acetate are added. The biphasic mixture is cooled down to 0° C. and 10 % sulfuric acid is added dropwise until the pH value of the aqueous phase reaches 2.5. After separating the organic phase, the aqueous layer is extracted four times with 20 ml of ethyl acetate each, then the combined organic phase is washed with 30 ml of water. After drying the organic phase over anhydrous magnesium sulfate the solution is evaporated under reduced pressure to yield 13.9 g (95.8 %) of (2S)-2-methyl-3-rhodanidopropionic acid, $[\alpha]_D^{25}$ −68° (c=1, chloroform).

The extracted aqueous phases remaining from the steps under A) and B) above are combined and rendered alkaline by adding 20 % aqueous sodium hydroxide solution. After extracting three times with 200 ml of benzene each the combined organic solution is dried over anhydrous magnesium sulfate and evaporated. In this way about 90 % of the (αS)-methyl-benzomethanamine used can be recovered.

Preparation of 1-[(2S)-2-methyl-1-oxo-3rhodanidopropyl]-L-proline.

A solution of 29.4 g of (2S)-2-methyl-3-rhodanidopropionic acid in 400 ml of methylene chloride is cooled to −10° C. and after adding dropwise 17.38 g of pyridine, 30.05 g of isobutyl chloroformate are dropwise added during 10 minutes. After maintaining the suspension obtained between −5° C. and −10° C. for 10 minutes, first 23.06 g of L-proline and then 15.8 g of pyridine are added during 5 minutes. The suspension is kept at −5° C. for one hour, thereafter it is allowed to warm to room temperature. After portionwise adding 300 ml of water the reaction mixture is cooled to 0° C. and the pH value is adjusted to 1 by adding 10 % sulfuric acid.

After separating the organic phase the aqueous layer is extracted four times with 400 ml of methylene chloride each and the combined organic phase is washed with 400 ml of water. The organic phase is dried over anhydrous magnesium sulfate, evaporated under reduced pressure and 50 ml of ether are added to the residue. A crystalline suspension is obtained which is maintaineed at 0° C. for a few hours. The crystals precipitated are filtered and washed with cooled benzene to give the aimed product in a yield of 29.13 g (60.1 %), m.p.: 136°-136° C., $[\alpha]_D^{20}$ −266.4° (c=1, chloroform). IR spectrum (KBr) $\nu cm^{-1}$: 2153 (NCS), 1727 (CO, acid).

We claim:

1. A process for the preparation of 1-[(2S)-3-mercapto-2-methyl-1-oxopropyl]-L-proline of the formula (I)

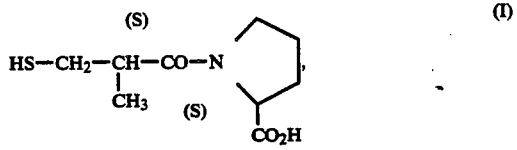

which comprises hydrogenolysing 1-[(2S)-2-methyl-1-oxo-3-rhodanidopropyl]-L-proline of the formula (II)

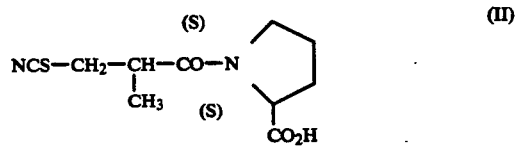

in an inert solvent in the presence of a hydrogenating catalyst at a temperature of 50° to 120° C. under a pressure of $10^5$ to $10^7$ Pa.

2. A process as claimed in claim 1, which comprises carrying out the hydrogenation at a temperature of 70° to 90° C.

3. A process as claimed in claim 1, which comprises carrying out the hydrogenation under a pressure of $(5-6) \times 10^5$ Pa.

4. A process as claimed in claim 1, which comprises using palladium-on-charcoal as catalyst.

5. 1-(2-Methyl)-1-oxo-3-rhodaniodopropyl)proline.

* * * * *